United States Patent

Baranski et al.

[11] Patent Number: 5,789,357
[45] Date of Patent: Aug. 4, 1998

[54] DITHIOCARBAMYL CARBOXYLIC ACIDS AND THEIR USE AS MULTIFUNCTIONAL ADDITIVES FOR LUBRICATING OILS

[75] Inventors: John R. Baranski, Southington, Conn.; Cyril A. Migdal, Pleasant Valley, N.Y.; Robert G. Rowland, Woodbridge, Conn.

[73] Assignee: Uniroyal Chemical Company, Inc., Middlebury, Conn.

[21] Appl. No.: 782,203

[22] Filed: Jan. 10, 1997

[51] Int. Cl.$^6$ ............................................. C10M 135/18
[52] U.S. Cl. ............................................. 508/444
[58] Field of Search ............................................. 508/444

[56] References Cited

U.S. PATENT DOCUMENTS

| | | | |
|---|---|---|---|
| 5,462,683 | 10/1995 | Kinoshita et al. | 508/444 |
| 5,512,190 | 4/1996 | Anderson et al. | 548/141 |
| 5,514,189 | 5/1996 | Farng et al. | 44/383 |

OTHER PUBLICATIONS

Chemical Abstracts vol. 116:20603, 1992, month unavailable.
CA Registry Nos. 93414-95-1; 81994-76-5;14394-10-6;7629-44-9;769-43-8; date unavailable.

*Primary Examiner*—Jacqueline V. Howard
*Attorney, Agent, or Firm*—Raymond D. Thompson

[57] ABSTRACT

Dithiocarbamyl carboxylic acids, useful as multifunctional additives for lubricating oils, possess the general formula:

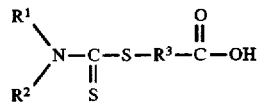

wherein $R^1$ and $R^2$ each independently is a hydrocarbyl group of from 1 to about 60 carbon atoms and $R^3$ is a divalent alkylene group of from 1 to about 20 carbon atoms.

14 Claims, No Drawings

DITHIOCARBAMYL CARBOXYLIC ACIDS AND THEIR USE AS MULTIFUNCTIONAL ADDITIVES FOR LUBRICATING OILS

BACKGROUND OF THE INVENTION

This invention relates to dithiocarbamyl carboxylic acids and their use as multifunctional additives for lubricating oils.

Zinc dialkyldithiophosphates (ZDDPs) have been used as anti-fatigue, anti-wear, extreme pressure and friction modifying additives for lubricating oils for many years. However, they are subject to several drawbacks owing to their zinc and phosphorus contents. During operation of an internal combustion engine, lubricating oil enters the combustion chambers by means such as clinging to cylinder walls as the piston makes its down stroke. When phosphorus-containing lubricating oil compositions enter the combustion reaction, phosphorus enters the exhaust stream where it acts as a catalyst poison thus shortening the useful life of the catalytic converter. In addition, the presence of zinc contributes to the emission of particulates in the exhaust.

In view of the aforementioned shortcomings with the known zinc and phosphorus-containing additives, efforts have been made to provide lubricating oil additives which contain neither zinc nor phosphorus. Illustrative of non-zinc (i.e., ashless), non-phosphorus-containing lubricating oil additives are the reaction products of 2,5-dimercapto-1,3,4-thiadiazole and unsaturated mono-, di- and tri-glycerides of U.S. Pat. No. 5,512,190 and the dialkyl dithiocarbamate-derived organic ethers of U.S. Pat. No. 5,514,189.

SUMMARY OF THE INVENTION

In accordance with the present invention, dithiocarbamyl carboxylic acids for lubricant additives are provided having the general formula

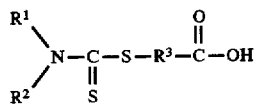

wherein $R^1$ and $R^2$ each independently is a hydrocarbyl group of from 1 to about 60 carbon atoms and $R^3$ is a divalent alkylene group of from 1 to about 20 carbon atoms.

The foregoing dithiocarbamyl carboxylic acids are useful as ashless anti-fatigue, anti-wear and extreme pressure additives for lubricating oils where they can be employed in total or partial replacement of the ZDDPs currently in use.

DESCRIPTION OF THE PREFERRED EMBODIMENTS

The dithiocarbamyl carboxylic acids of this invention can be prepared in accordance with the following sequence of reaction steps:

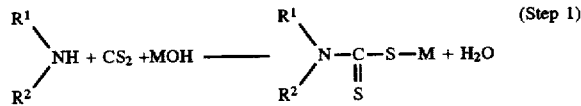
(Step 1)

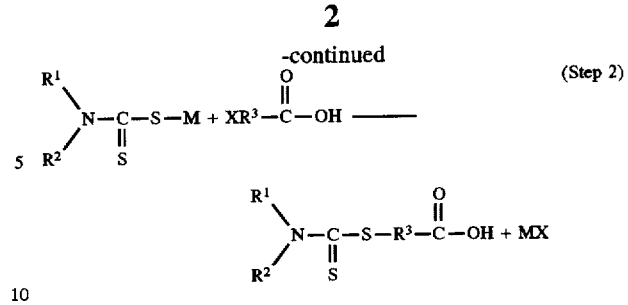

In the foregoing sequence of reactions, $R^1$, $R^2$ and $R^3$ are each as defined above, M is alkali metal and X is halogen.

In step 1, dihydrocarbylamine $R^1R^2NH$ is reacted with an equimolar amount of alkali metal hydroxide MOH and carbon disulfide, the latter preferably in slight molar excess, to provide an alkali metal di(hydrocarbyl)thiocarbamate intermediate $R^1R^2NCSSM$. Useful dihydrocarbylamines are those in which hydrocarbyl groups $R^1$ and $R^2$ are selected from among alkyl, cycloalkyl, alkaryl and aralkyl groups of up to about 60 carbon atoms. Preferred dihydrocarbylamine reactants are dialkylamines in which each alkyl group contains from about 2 to about 30, and more preferably from about 4 to about 24, carbon atoms. The alkali metal hydroxide is conveniently aqueous sodium hydroxide and the reaction is advantageously conducted in a suitable solvent with water and/or a lower alkanol such as methanol, ethanol, propanol, 2-propanol, isopropanol, n-butanol, sec-butanol or t-butanol. Isopropanol being preferred for this purpose.

In Step 2, an equimolar amount of haloalkanoic acid, e.g., 3-chloropropionic acid, is added to the reaction medium of Step 1 where it reacts with alkali metal di(hydrocarbyl) thiocarbamate intermediate to provide product dithiocarbamyl carboxylic acid.

The dithiocarbamyl carboxylic acids of this invention can be utilized in lubricating oil compositions in amounts which impart significant anti-wear characteristics to the oils as well as reducing the friction of engines operating with the oils. Concentrations of from about 0.001 to about 10 weight percent based on the total weight of the lubricating oil composition can be used. Preferably, the concentration is from about 0.1 to about 3 weight percent.

In general, mineral oils, both paraffinic, naphthenic and mixtures thereof, including those oils defined as American Petroleum Institute Groups I, II, and III, can be employed as the lubricant vehicle, and can be of any suitable lubricating viscosity range, as for example, from about 2 cSt at 100° C. to about 1,000 cSt at 100° C. and preferably from about 2 to about 100 cSt at 100° C. These oils can have viscosity indexes preferably ranging to about 180. The average molecular weights of these oils can range from about 250 to about 800. Where synthetic oils are employed, they can include, but are not limited to, polyisobutylene, polybutenes, hydrogenated polydecenes, polypropylene glycol, polyethylene glycol, trimethylpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, and phenoxy phenylethers.

It is to be understood, however, that the lubricating oil compositions herein can also contain other materials. For example, corrosion inhibitors, extreme pressure agents, detergents, dispersants, antiwear agents, antioxidants, antifoamants, friction modifiers, low temperature properties modifiers and the like can be used. Examples of these materials include metallic phenates or sulfonates, alkylated diphenylamines, polymeric succinimides, non-metallic or metallic phosphorodithioates and the like. These materials do not detract from the value of the compositions of this invention, rather the materials serve to impart their customary properties to the particular compositions in which they are incorporated.

The following examples are illustrative of the preparation of the dithiocarbamyl carboxylic acids of this invention and their use as anti-fatigue, anti-wear and extreme pressure additives for lubricating oils.

EXAMPLE 1

This example illustrates the preparation of 3-(N,N-diamyldithiocarbamyl)-propionic acid.

Step 1: Preparation of sodium diamyldithiocarbamate intermediate

To a 250 mL 3-neck round bottom reaction flask equipped with an overhead stirrer, a thermocouple probe, a reflux condenser, a Claisen adapter, and a 25 mL addition funnel, 30.0 g (0.19 mol) of diamyl amine, 15.3 g of a 50 weight percent NaOH solution (0.19 mol NaOH) and 100 mL reagent 2-propanol was added. 12.5 mL (0.21 mol) carbon disulfide was charged to the addition funnel. Carbon disulfide was added over a half-hour period. The reaction temperature was maintained at 25°–30° C. The product was post-reacted at 25° C. for 1 hour.

Step 2: Preparation of product 3-(N,N-diamyldithiocarbamyl)-propionic acid 20.6 g (0.19 mol) of 3-chloropropionic acid was added to the reactor containing the Step 1 product. The reactor was heated to reflux with the pot temperature maintained at 70° C. for 3 hours. The reaction temperature was then reduced to 30° C. The product was transferred to a 500 mL separatory funnel combined with 100 mL reagant hexanes and washed four times with 500 mL portions of 60° C. water. The volatiles were removed using a rotary evaporator. 33.1 g of a light yellow low viscosity clear liquid product was obtained.

EXAMPLE 2

This example illustrates the preparation of 3-(N,N-ditetradecyldithiocarbamyl)-propionic acid.

Step 1: Preparation of sodium di(tetradecyl) dithiocarbamate intermediate

To a 500 mL 3-neck round bottom reaction flask equipped with an overhead stirrer, a thermocouple probe, a reflux condenser, a Claisen adapter, and a 25 mL addition funnel, 82.0 g (0.20 mol) of dicoco amine (Armeen 2 C, AKZO), 16.2 g of a 50 weight percent NaOH solution (0.20 mol NaOH) and 100 mL reagent 2-propanol was added. 13.0 mL (0.22 mol) carbon disulfide was charged to the addition funnel. The reactor was heated to 50° C. Once the amine was dissolved, the reaction temperature was reduced to 40° C. Carbon disulfide was added over a half-hour period. The reaction temperature was lowered over the course of the carbon disulfide addition from 40° C. to 30° C. The product was post-reacted at 30° C. for 1 hour.

Step 2: Preparation of product 3-(N,N-ditetradecyldithiocarbamyl)-propionic acid 21.7 g (0.20 mol) of 3-chloropropionic acid was added to the reactor containing the Step 1 product. The reactor was heated to reflux with the pot temperature maintained at 74° C. for 3 hours. The reaction temperature was then reduced to 30° C. The product was transferred to a 1000 mL separatory funnel, combined with 100 mL reagant hexanes, and washed four times with 300 mL portions of 60° C. water. The volatiles were removed using a rotary evaporator. 98.8 g of a light yellow product was obtained having a consistency of petroleum jelly at room temperature.

EXAMPLE 3

The anti-wear properties of the dithiocarbamyl carboxylic acids of Example 1, Example 2 and those of a conventional zinc dialkyldithiophosphate in two fully formulated lubricating oils were determined employing the Four-Ball Wear Test of ASTM D 4172. The two lubricating oils, Formulations A and B of Table 2 below, also contained 1 wt. % cumene hydroperoxide. Table 1 below sets forth the numerical value of the test results (Average Wear Scar Diameter, mm). This value decreases with an increase in anti-wear effectiveness.

TABLE 1

Four-Ball Wear Results

| Anti-wear Additive | Motor Oil Formulation | Average Wear Scar Diameter, mm |
|---|---|---|
| 3-(N,N-diamyldithiocarbamyl)-propionic acid | A | 0.54 |
| 3-(N,N-ditetradecyldithiocarbamyl)-propionic acid | A | 0.54 |
| No anti-wear additive | A | 0.93 |
| Zinc dialkyldithiophosphate | A | 0.46 |
| 3-(N,N-diamyldithiocarbamyl)-propionic acid | B | 0.64 |
| 3-(N,N-ditetradecyldithiocarbamyl)-propionic acid | B | 0.64 |
| No anti-wear additive | B | 0.98 |
| Zinc dialkyldithiophosphate | B | 0.53 |

TABLE 2

SAE 10W-30 Motor Oil Formulations

| Formulation A | wt. % | Formulation B | wt. % |
|---|---|---|---|
| Solvent Neutral 100 | 22.8 | Solvent Neutral 100 | 22.8 |
| Solvent Neutral 150 | 60 | Solvent Neutral 150 | 60 |
| Succinimide Dispersant | 7.5 | Succinimide Dispersant | 7.5 |
| Overbased Calcium Phenate Detergent | 2.0 | Overbased Calcium Sulfonate Detergent | 2.0 |
| Neutral Calcium Sulfonate Detergent | 0.5 | Neutral Calcium Sulfonate Detergent | 0.5 |
| Antioxidant | 0.5 | Antioxidant | 0.5 |
| Rust Inhibitor | 0.1 | Rust Inhibitor | 0.1 |
| Pour Point Depressant | 0.1 | Pour Point Depressant | 0.1 |
| OCP VI Improver | 5.5 | OCP VI Improver | 5.5 |
| Anti-wear Additive[1] | 1.0 | Anti-wear Additive | 1.0 |

[1]In the case where no anti-wear additive was employed, solvent neutral 150 was used in place of the additive at 1.0 weight percent.

As the data in Table 1 show, the dithiocarbamyl carboxylic acids of this invention performed nearly as well as the known zinc dialkyldithiophosphate additive in both motor oil formulations.

What is claimed is:

1. A lubricating oil composition comprising a lubricating oil and a functional property-improving amount of at least one dithiocarbamyl carboxylic acid of the general formula

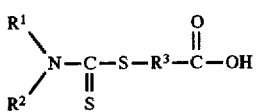

wherein $R^1$ and $R^2$ each independently is a hydrocarbyl group of from 1 to about 60 carbon atoms and $R^3$ is a divalent alkylene group of from 1 to about 20 carbon atoms.

2. The lubricating oil composition of claim 1 wherein $R^1$ and $R^2$ each is an alkyl group of from about 2 to about 30 carbon atoms.

3. The lubricating oil composition of claim 1 wherein $R^1$ and $R^2$ each is an alkyl group of from about 4 to about 24 carbon atoms.

4. The lubricating oil composition of claim 1 wherein $R^3$ contains from 2 to about 12 carbon atoms.

5. The lubricating oil composition of claim 1 wherein $R^1$ and $R^2$ each is an alkyl group of from about 4 to about 24 carbon atoms and $R^3$ contains from 2 to about 12 carbon atoms.

6. The lubricating oil composition of claim 1 wherein the functional property-improving amount of at least one dithiocarbamyl carboxylic acid is 3-(N,N-diamyldithiocarbamyl)-propionic acid.

7. The lubricating oil composition of claim 1 wherein the functional property-improving amount of at least one dithiocarbamyl carboxylic acid is 3-(N,N-ditetradecyldithiocarbamyl)-propionic acid.

8. A method for improving at least one functional property of a lubricating oil which comprises adding to the lubricating oil a functional property-improving amount of at least one dithiocarbamyl carboxylic acid of the general formula

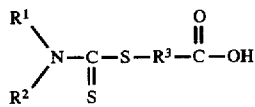

wherein $R^1$ and $R^2$ each independently is a hydrocarbyl group of from 1 to about 60 carbon atoms and $R^3$ is a divalent alkylene group of from 1 to about 20 carbon atoms.

9. The method of claim 8 wherein $R^1$ and $R^2$ each is an alkyl group of from about 2 to about 30 carbon atoms.

10. The method of claim 8 wherein $R^1$ and $R^2$ each is an alkyl group of from about 4 to about 24 carbon atoms.

11. The method of claim 8 wherein $R^3$ contains from 2 to about 12 carbon atoms.

12. The method of claim 8 wherein $R^1$ and $R^2$ each is an alkyl group of from about 4 to about 24 carbon atoms and $R^3$ contains from 2 to about 12 carbon atoms.

13. The method of claim 8 wherein the functional property-improving amount of at least one dithiocarbamyl carboxylic acid is 3-(N,N-diamyldithiocarbamyl)-propionic acid.

14. The method of claim 8 wherein the functional property-improving amount of at least one dithiocarbamyl carboxylic acid is 3-(N,N-ditetradecyldithiocarbamyl)-propionic acid.

* * * * *